(12) United States Patent
Yang

(10) Patent No.: US 8,235,523 B2
(45) Date of Patent: Aug. 7, 2012

(54) EYE COVERING

(75) Inventor: Shun-Tien Yang, Tainan Hsien (TW)

(73) Assignee: All-Logic Int. Co., Ltd., Tainan Hsien (TW)

( * ) Notice: Subject to any disclaimer, the term of this patent is extended or adjusted under 35 U.S.C. 154(b) by 333 days.

(21) Appl. No.: 12/784,815

(22) Filed: May 21, 2010

(65) Prior Publication Data

US 2011/0122364 A1 May 26, 2011

(30) Foreign Application Priority Data

Nov. 26, 2009 (TW) ................................ 98222167 U

(51) Int. Cl.
*G02C 1/00* (2006.01)
(52) U.S. Cl. .................... 351/43; 351/62; 2/429; 2/436; 2/441
(58) Field of Classification Search .................... 351/43, 351/62, 156, 47, 57; 2/429, 436, 441, 435, 2/426, 452, 448, 430, 431
See application file for complete search history.

(56) References Cited

U.S. PATENT DOCUMENTS

| 2,864,088 A | * | 12/1958 | Gongoll | 2/441 |
| 5,018,223 A | * | 5/1991 | Dawson et al. | 2/436 |
| 5,564,132 A | * | 10/1996 | Kuo | 2/430 |
| 5,802,622 A | * | 9/1998 | Baharad et al. | 2/434 |
| 7,257,848 B2 | * | 8/2007 | Chiang | 2/448 |

* cited by examiner

*Primary Examiner* — Hung Dang
(74) *Attorney, Agent, or Firm* — Marger Johnson & McCollom PC

(57) ABSTRACT

An eye covering includes an outer frame for surrounding a facial area around a wearer's eyes. The outer frame includes a lens frame that has a first upright wall. The first upright wall is formed with at least one first slot. The eye covering further includes a lens engaged in the lens frame. The lens includes at least one engaging piece that extends rearward to engage the first slot. The eye covering also includes an inner frame having a lining portion that is disposed to line a peripheral portion of the lens and that is disposed between the peripheral portion of the lens and the outer frame.

17 Claims, 6 Drawing Sheets

EYE COVERING

CROSS-REFERENCE TO RELATED APPLICATION

This application claims priority to Taiwanese application no. 098222167, filed on Nov. 26, 2009, the contents of which are incorporated by reference.

BACKGROUND OF THE INVENTION

1. Field of the Invention

The invention relates to an eye covering, more particularly to an eye covering with a firm construction.

2. Description of the Related Art

An eye covering may be used to perform optical correction, sun-shading, or eye protection. The conventional eye covering may be assembled without sufficient structure to withstand forces from various directions, causing the eye covering to fail to perform its intended function.

SUMMARY OF THE INVENTION

An object of the present invention is to provide an eye covering with a firm construction.

Accordingly, an eye covering of this invention comprises an outer frame for surrounding a facial area around a wearer's eyes. The outer frame includes a lens frame that has a first upright wall. The first upright wall is formed with at least one first slot. The eye covering further includes a lens engaged in the lens frame. The lens includes at least one engaging piece that extends rearward to engage the first slot. The eye covering also includes an inner frame having a lining portion that is disposed to line a peripheral portion of the lens and that is disposed between the peripheral portion of the lens and the outer frame.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

Figure 1:
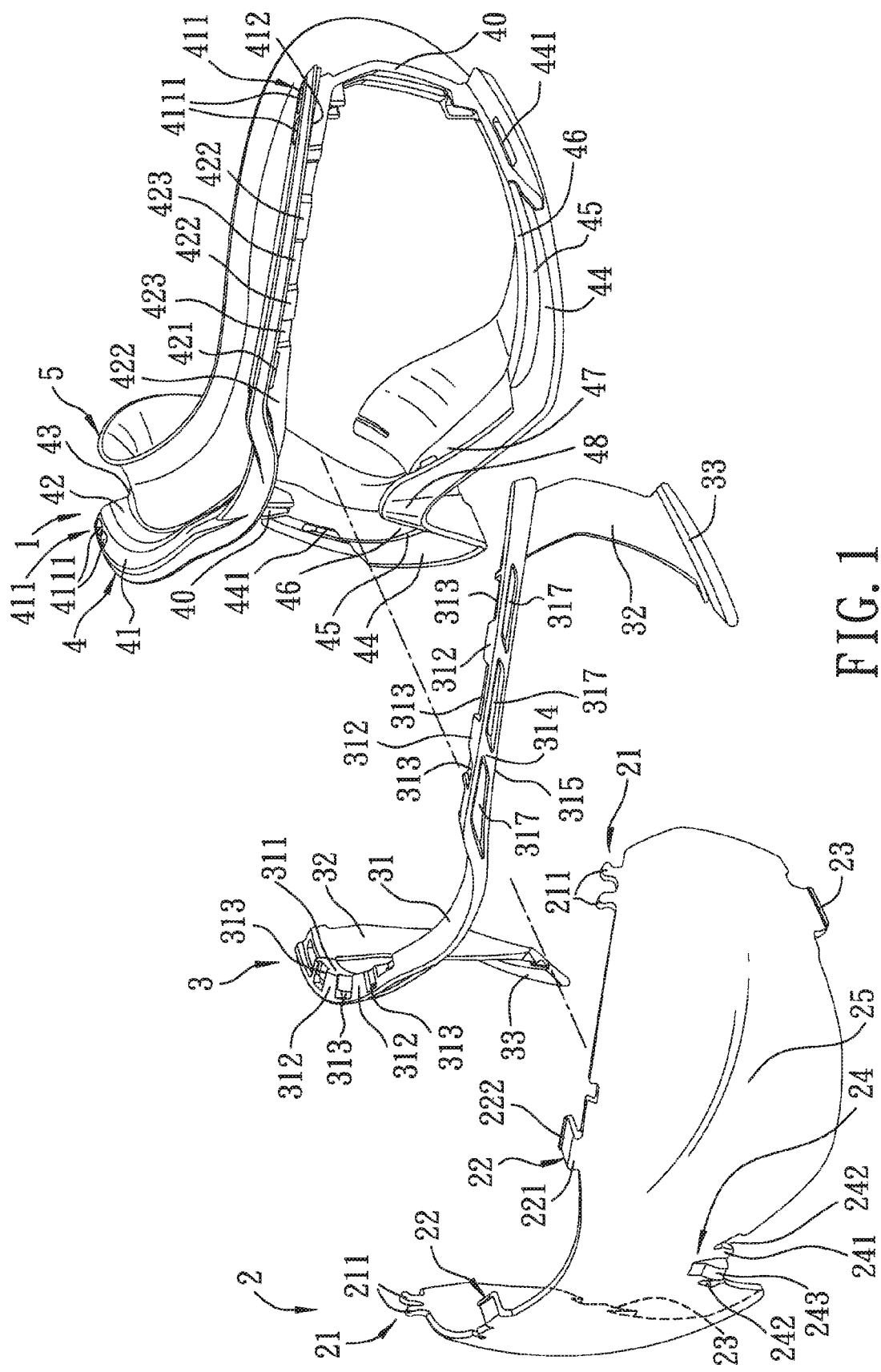
FIG. 1 is an exploded perspective view of an eye covering, according to the preferred embodiment of the present invention.

Referring to FIGS. 1, 2, 3, and 4, the preferred embodiment of an eye covering according to the present invention is shown to include an outer frame 1, a lens 2 engaged in the front of the outer frame 1, and an inner frame 3. The lens 2 includes a lens body 25 having a top edge portion and two lateral bottom edge portions. The inner frame 3 forms a cushion between the top edge portion of the lens body 25 of the lens 2 and the outer frame 1.

In practice, the eye covering can include a resilient strap (not shown) mounted between lateral end parts of the outer frame 1, or a pair of temples (not shown), each of which is mounted on a respective lateral end part of the outer frame 1. Because these are not the primary features of this invention, they are not further discussed.

The outer frame 1 is adapted for surrounding a facial area around a wearer's eyes. The outer frame 1 includes a hollow lens frame 4 disposed at a front side of the outer frame 1 in which the lens 2 is embedded. The outer frame 1 further includes gasket 5 extending rearwardly and integrally from a rear side of the lens frame 4.

The lens frame 4 includes an upper encasing wall 41 disposed at an upper part 7 of the lens frame 4 and disposed above the top edge portion of the lens body 25. The lens frame 4 further includes a first upright wall 42 that extends and curves downwardly from a rear edge of the upper encasing wall 41 (i.e., the upper encasing wall 41 extends forward from an upper part of the first upright wall 42), and an upper connecting wall 43 that extends and curves rearwardly from a lower part of the first upright wall 42. The upper connecting wall 43 is connected to the gasket 5.

The lens frame 4 also includes a pair of lower encasing walls 44, each disposed below a corresponding one of the lateral bottom edge portions of the lens body 25, a pair of second upright walls 45 each extending and curving upward from a rearward part of a corresponding one of the lower encasing walls 44, and a pair of lower connecting walls 46 each extending and curving rearward from an upper part of a corresponding one of the second upright walls 45 and being connected to the gasket 5.

The lens frame 4 further includes a middle support wall 47 in the form of a downwardly opening generally U-shaped body. The middle support wall 47 is connected to the lower encasing walls 44, the second upright walls 45, and the lower connecting walls 46. The lens frame 4 also includes a front upwardly extending wall 48 that is connected to a front edge of the middle support wall 47 and that has opposite lateral ends connected to the lower encasing walls 44, respectively. The front upwardly extending wall 48 has a rear side formed with a guide channel 481 that may be deeper at a bottom end portion than at a top end portion thereof. The lens frame 4 also includes a rear protruding wall 49 that extends upward from a top section of the middle support wall 47 and that is disposed spacedly behind the front upwardly extending wall 48.

The top section of the middle support wall 47 is formed with a middle engaging hole 471 disposed between the front upwardly extending wall 48 and the rear protruding wall 49. The front upwardly extending wall 48 cooperates with the rear protruding wall 49 to form an engaging channel 473 that is in spatial communication with the middle engaging hole 471. The front upwardly extending wall 48 may be inclined rearwardly relative to the front edge of the middle support wall 47, and the engaging channel 473 may have a narrow top and a wide bottom. The middle support wall 47 further includes a pair of insert blocks 472 each extending upward from the top section of the middle support wall 47 at a corresponding lateral side of the middle engaging hole 471.

The lens frame 4 further includes a pair of lateral connecting walls 40, each of which extends downward from a respective one of the lateral end parts of the upper connecting wall 43 and is connected to a respective one of the lower connecting walls 46.

The upper encasing wall 41 of the lens frame 4 has a pair of lateral end parts each formed with a hole unit 411. Each hole unit 411 includes two top holes 4111 and a brace 4112 that separates the two top holes 4111.

The first upright wall 42 is formed with a pair of first slots 421 that are horizontally spaced apart and disposed between the hole units 411. Each of the lower encasing walls 44 has a lateral end part formed with a second slot 441. In variations of the preferred embodiment, additional or fewer first slots 421 or second slots 441 may be implemented. In the variations, each of the first slots 421 may be located on any part of the first upright wall 42, and each of the second slots 441 may be located on any part of the lower encasing walls 44.

Each lateral end part of the upper connecting wall 43 is connected to a corresponding lateral connecting wall 40 that is in turn connected to a corresponding lower connecting wall 46. The upper connecting wall 43, the lateral connecting walls 40, and the lower connecting wall 46 are integrally connected to the gasket 5. The gasket 5 is a resilient pad that is softer than the lens frame 4 for abutting against a facial area around the wearer's eyes.

The lens 2 includes the lens body 25 engaged in the lens frame 4 of the outer frame 1. The lens body 25 includes top and bottom edge portions that are disposed between the upper encasing wall 41 and the lower encasing walls 44. The lens body 25 further includes left and right lateral peripheral portions that are disposed at a front side of the lateral connecting walls 40. The center part of the bottom edge of the lens body 25 is a downward opening indentation.

The lens body 25 of the lens 2 is formed with two engaging units 21 that each extend upwardly from the top edge portion of the lens body 25 and through a lining portion 31 (to be described hereinafter) of the inner frame 3 to engage a corresponding hole unit 411 in a corresponding lateral end part of the upper encasing wall 41. Each engaging unit 21 is formed with a pair of prongs 211, each received in a corresponding top hole 4111 of a corresponding hole unit 411 with a corresponding brace 4112 of the corresponding hole unit 411 received between the prongs 211. In variations of the preferred embodiment, the number of engaging units 21 and hole units 411 may be increased or decreased.

The lens 2 further includes a pair of engaging pieces 22 that extend upwardly and bend rearwardly from the top edge portion of the lens body 25 to engage the first slots 421 correspondingly. Each engaging piece 22 is formed with an L-shape, and includes a vertical support 221 that extends upward from the top edge portion of the lens body 25, and a first tab 222 extending horizontally and rearwardly from the vertical support 221 to engage horizontally the corresponding first slot 421. In variations of the preferred embodiment, the vertical support 221 and the first tab 222 may be formed in any shape enabling horizontal extension from the lens body 25 and engagement with the corresponding first slot 421.

The lens 2 further includes a pair of second tabs each extending downward from a corresponding lateral bottom edge portion of the lens body 25 to engage a corresponding second slot 441 in a corresponding one of the lower encasing walls 44.

The lens body 25 further includes a central bottom edge portion disposed between the lateral bottom edge portions and disposed between the front upwardly extending wall 48 and the rear protruding wall 49. The central bottom edge portion of the lens body 25 is formed with a pair of insert slots 242 that each engage a corresponding insert block 472.

The central bottom edge portion is formed with a middle engaging member 24 that extends into the middle engaging hole 471 via the engaging channel 473. The middle engaging member 24 is extended between the front upwardly extending wall 48 and the rear protruding wall 49. The middle engaging member 24 includes an insert board part 241 that is disposed between the insert slots 242. The insert board part 241 has a front side formed with a projection 243 that extends into the guide channel 481 and abuts against the front upwardly extending wall 48 for guiding extension of the middle engaging member 24 into the middle engaging hole 471.

The inner frame 3 includes the lining portion 31 that is disposed to line a peripheral portion of the lens 2, i.e., the top edge portion of the lens body 25, and that is disposed between the peripheral portion of the lens 2 and the upper encasing wall 41 of the lens frame 4. The lining portion 31 includes a bottom embedding face 315 that may be disposed opposite to a second abutment face 412 of the upper encasing wall 41 and that is formed with a bottom embedding channel 316 that opens downward, as best shown in FIG. 5.

The inner frame 3 further includes a pair of connecting liners 32 that each extend downwardly from a respective lateral end portion of the lining portion 31 and are each disposed between a corresponding lateral connecting wall 40 and the lens 2. The inner frame 3 further includes a pair of bottom liners 33, each formed at a bottom portion of a corresponding connecting liner 32 and disposed between a corresponding lateral bottom edge portion of the lens body 25 and a corresponding lower encasing wall 44.

Figure 3:
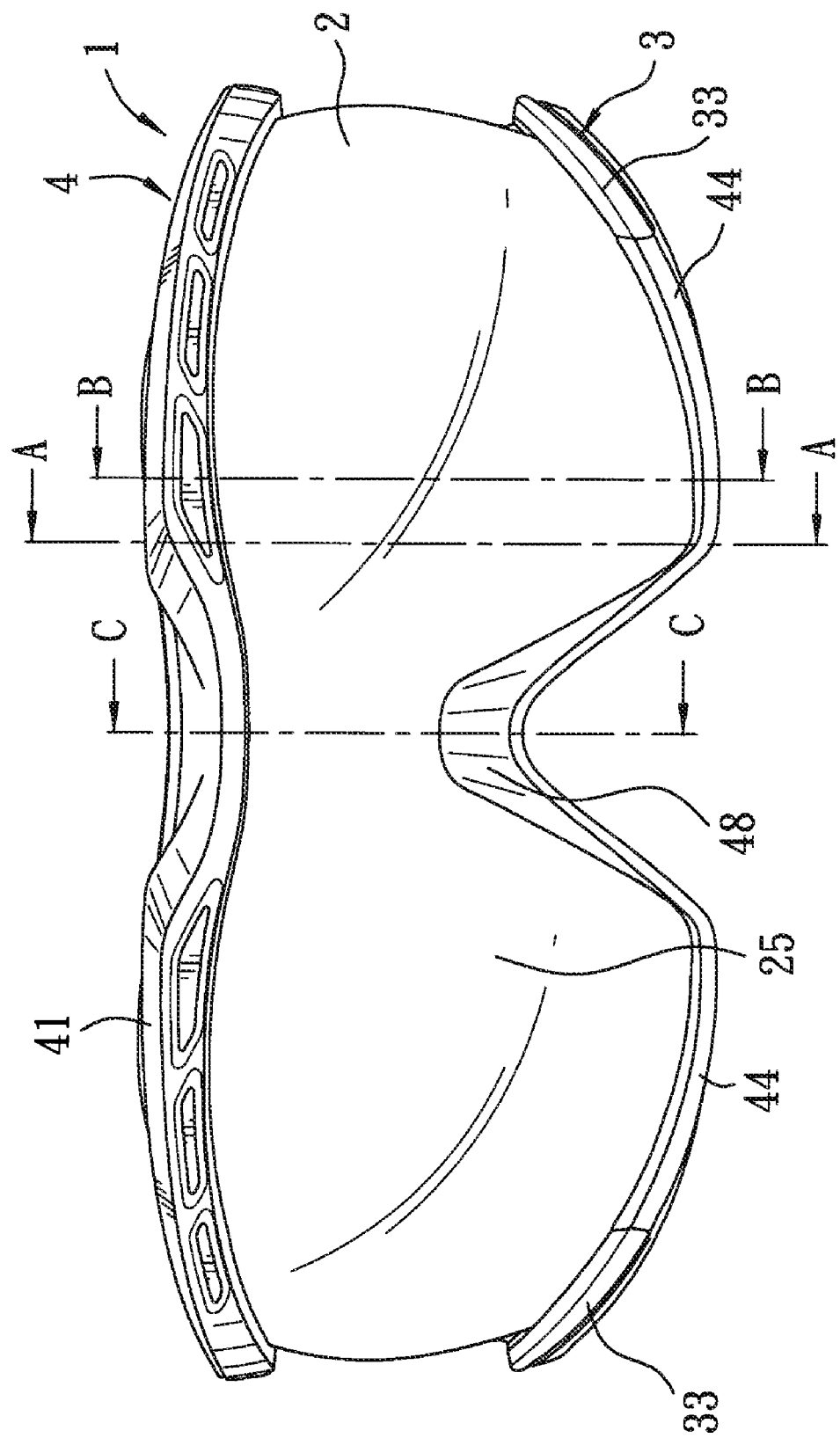
FIG. 3 is a front view of the preferred embodiment.
Figure 5:
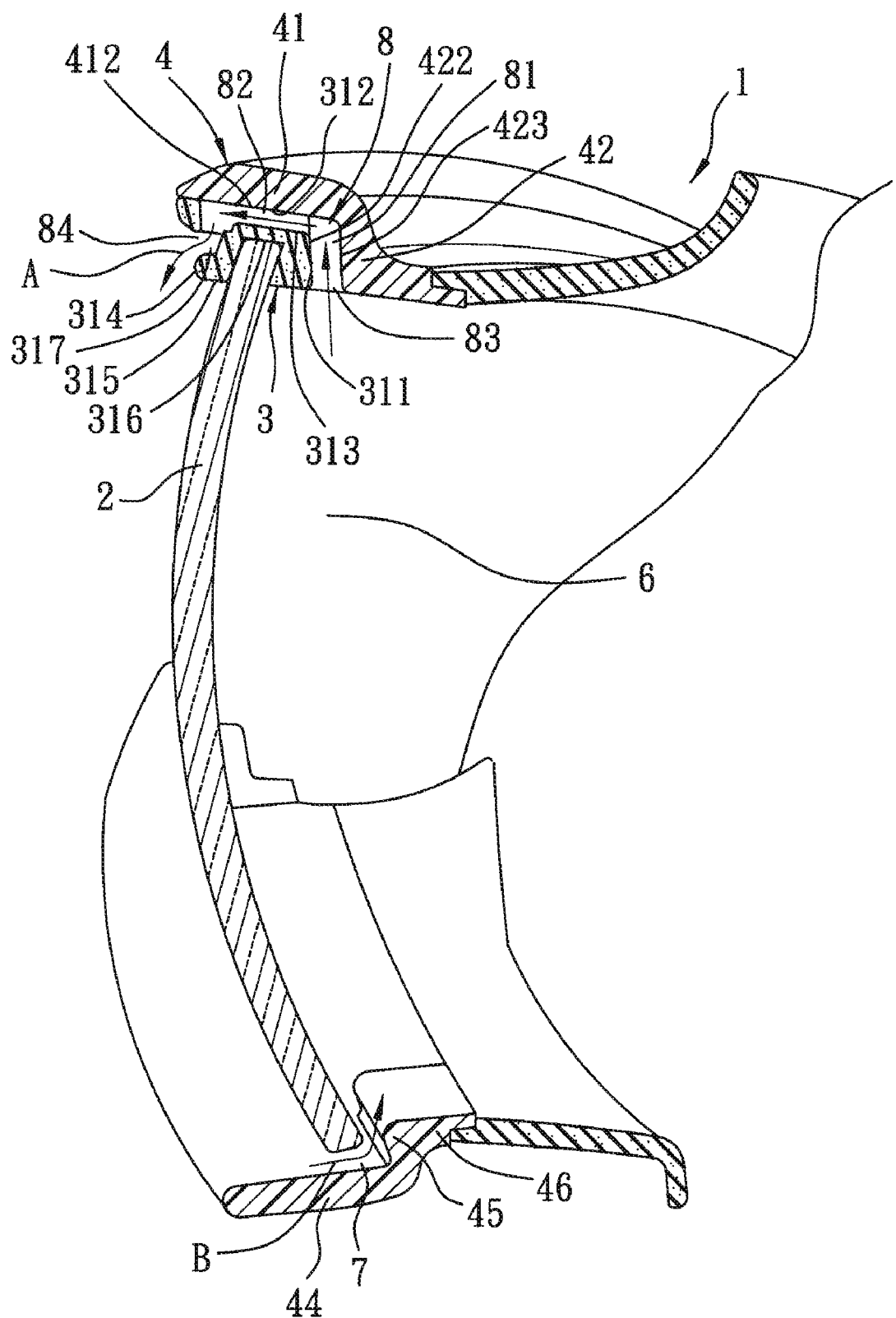
FIG. 5 is a fragmentary schematic sectional view taken along line B-B in FIG. 3, according to the preferred embodiment.

Referring to FIGS. 1, 3 and 5, the lens 2 and the outer frame 1 cooperate to define a covering space. Each of the lateral bottom edge portions of the lens body 25 cooperates with a corresponding one of the lower encasing walls 44, a corresponding one of the second upright walls 45, and a corresponding one of the lower connecting walls 46 to form a corresponding lower vent channel 7 that communicates spatially with the covering space 6 and the external environment of the eye covering.

The inner frame 3 and the outer frame 1 cooperate to define a plurality of vent channels 8 that each communicates spatially with the covering space 6 and the external environment of the eye covering. Each vent channel 8 includes an inlet 83 disposed at a rear side of the lens 2 and an outlet 84 disposed at a front side of the lens 2. A front face 314 of the lining portion 31 is formed with a plurality of vent openings 317 that correspond respectively to the vent channels 8 and that serve as the outlets 84 of the vent channels 8.

The lining portion 31 and the first upright wall 42 are formed with a rear passage-forming structure that forms rear passage portions 81 of the vent channels 8. Each of the rear passage portions 81 has the inlet 83 of the respective one of the vent channels 8. The lining portion 31 and the upper encasing wall 41 are formed with an upper passage-forming structure that forms upper passage portions 82 of the vent channels 8. Each of the upper passage portions 82 extends between a corresponding one of the rear passage portions 81 and a corresponding one of the vent openings 317.

In this embodiment, the rear passage-forming structure includes a plurality of first protruding face portions 422 that protrude from one side of one of the lining portion 31 and the first upright wall 42 toward the other one of the lining portion 31 and the first upright wall 42 and that are horizontally spaced apart from each other. The rear passage-forming structure further includes a plurality of first indented face portions 423 that are formed in the one side of the one of the lining portion 31 and the first upright wall 42, each of the first indented face portions 423 being adjacent to a corresponding one of the first protruding face portions 422 and being indented away from the other one of the lining portion 31 and the first upright wall 42. In addition, the rear passage-forming structure includes a first abutment face 311 that is disposed on one side of the other one of the lining portion 31 and the first upright wall 42, that abuts against the first protruding face portions 422, and that cooperates with the first indented face portions 423 to form the rear passage portions 81 of the vent channels 8. The first abutment face 311 is disposed at a rear portion of the lining portion 31 in this embodiment.

In this embodiment, the upper passage-forming structure includes a plurality of second protruding face portions 312 that protrude from one side of one of the lining portion 31 and the upper encasing wall 41 toward the other one of the lining portion 31 and the upper encasing wall 41 and that are horizontally spaced apart from each other. The upper passage-forming structure further includes a plurality of second indented face portions 313 that are formed in the one side of the one of the lining portion 31 and the upper encasing wall 41, each of the second indented face portions 313 being adjacent to a corresponding one of the second protruding face portions 312 and being indented away from the other one of the lining portion 31 and the upper encasing wall 41. The upper passage-forming structure also includes a second abutment face 412 that is disposed on one side of the other one of the lining portion 31 and the upper encasing wall 41, that abuts against the second protruding face portions 312, and that cooperates with the second indented face portions 313 to form the upper passage portions 82 of the vent channels 8. The second abutment face 412 is disposed at a bottom portion of the upper encasing wall 41 in this embodiment.

Figure 4:
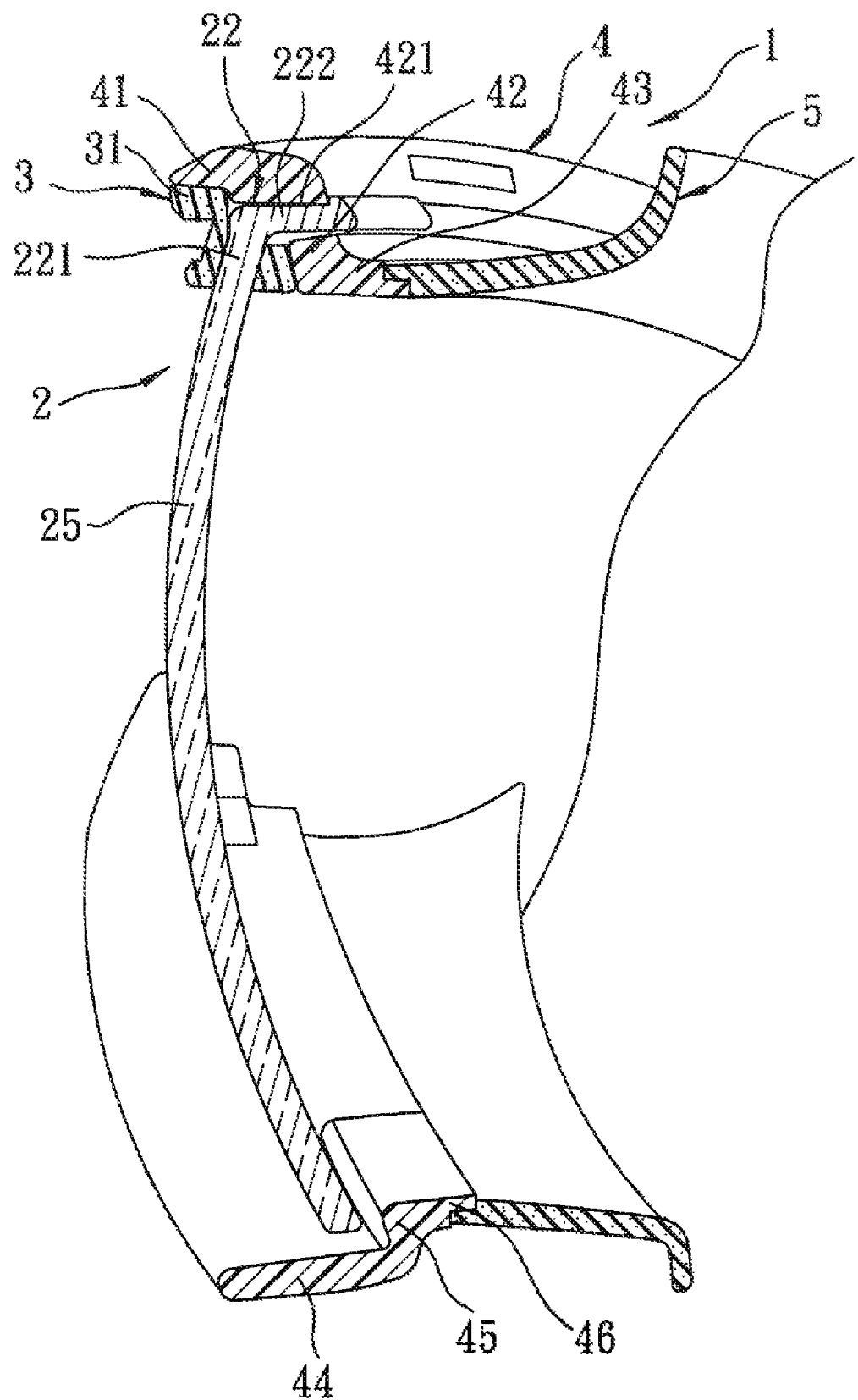
FIG. 4 is a fragmentary schematic sectional view taken along line A-A in FIG. 3, according to the preferred embodiment.

For assembly, referring to FIG. 1, the inner frame 3 is engaged with the top edge portion of the lens body 25. The lens 2 is then correspondingly placed in the lens frame 4 of the outer frame 1. Each engaging unit 21 is engaged with the corresponding hole unit 411, and each second tab 23 is extended into the corresponding second slot 441. As shown in FIG. 4, each engaging piece 22 is extended rearwardly into the corresponding first slot 421.

Figure 2:
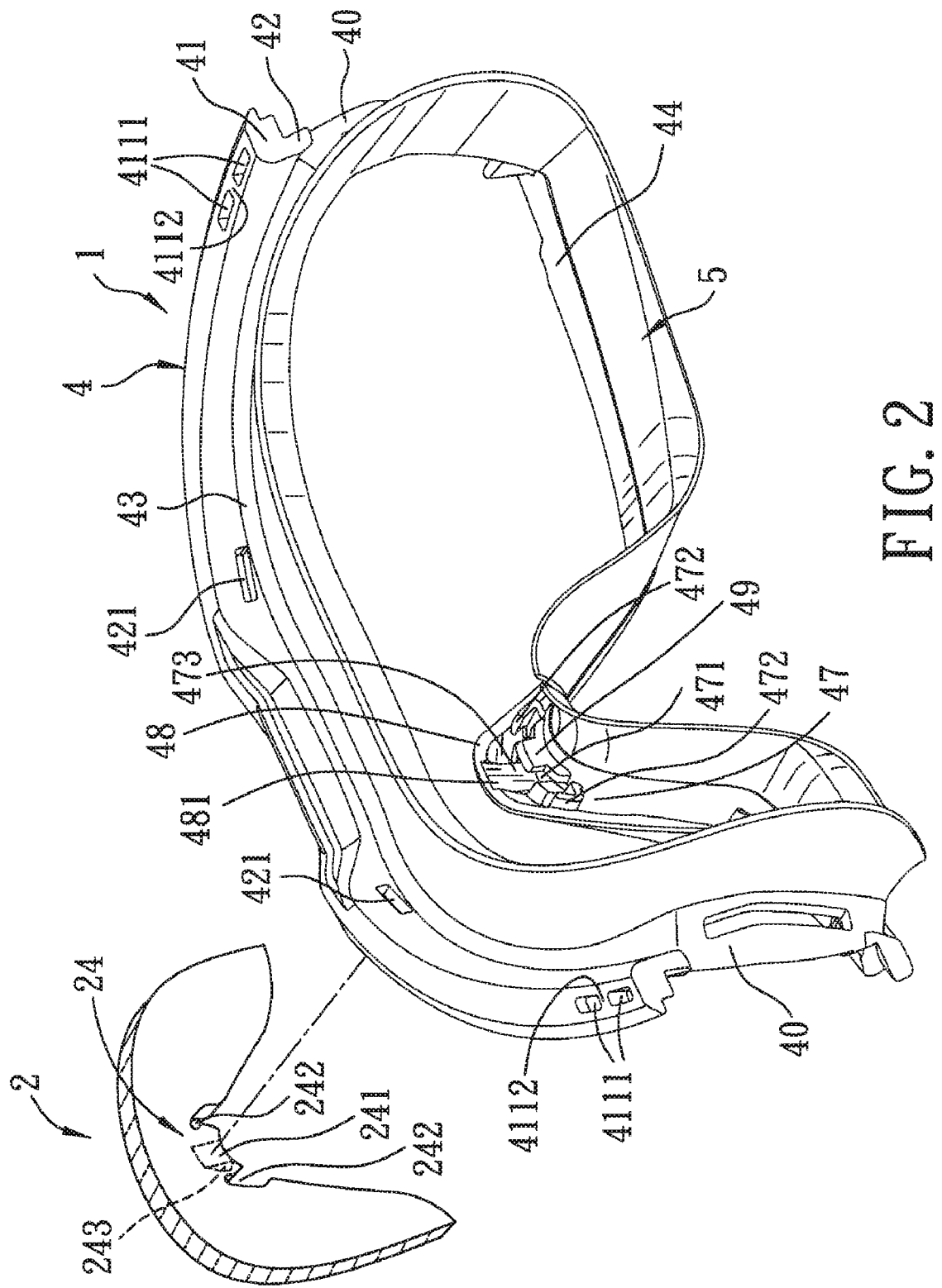
FIG. 2 is an exploded fragmentary rear perspective view of the preferred embodiment of the eye covering.
Figure 6:
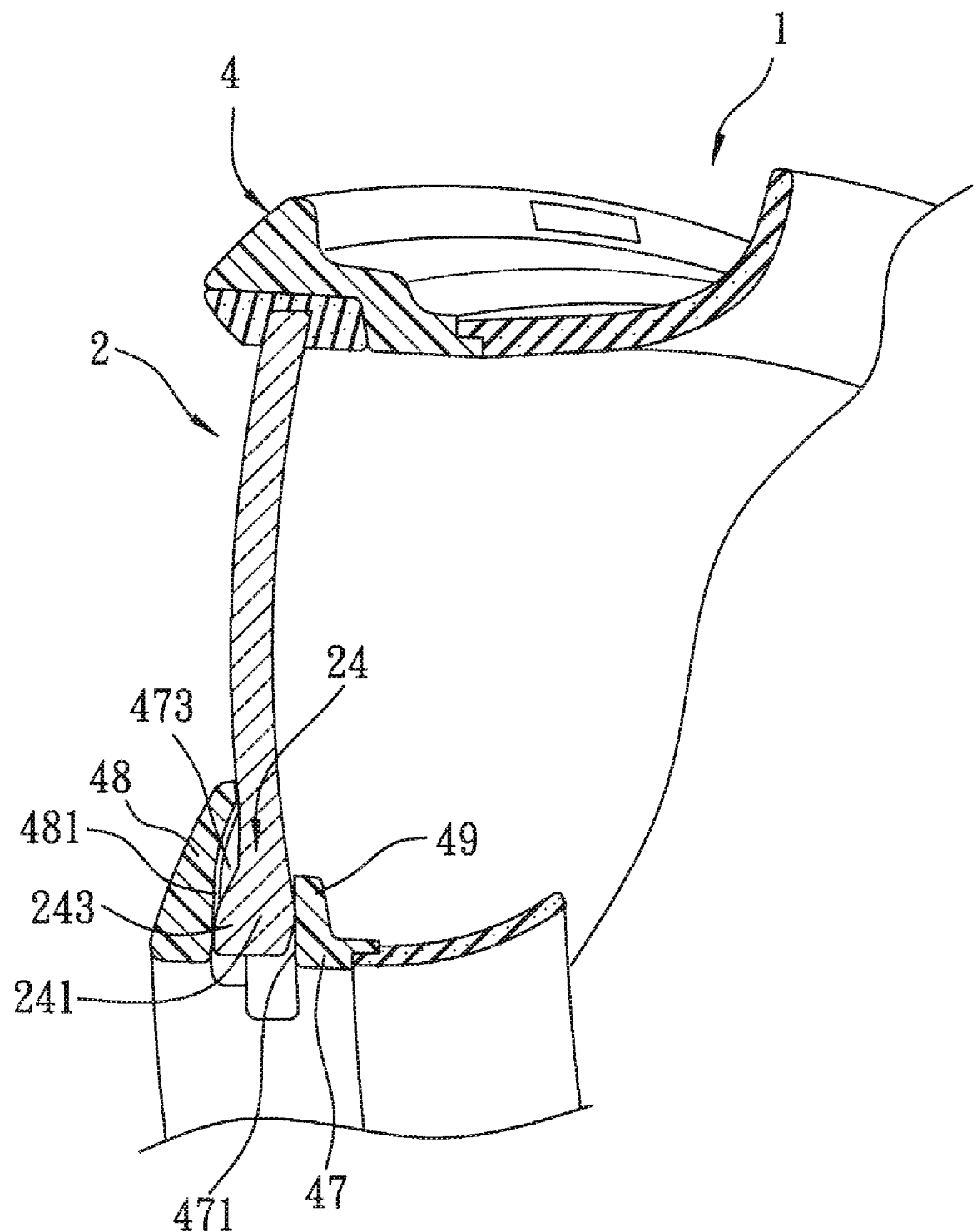
FIG. 6 is a fragmentary schematic sectional view taken along line C-C in FIG. 3, according to the preferred embodiment.

As shown in FIGS. 2 and 6, the middle engaging member 24 is extended between the front upwardly extending wall 48 and the rear protruding wall 49 such that the projection 243 is extended into the guide channel 481 and abutted against the front upwardly extending wall 48. The insert board part 241 is inserted into the engaging channel 473, permitting the bottom part thereof to engage the middle engaging hole 471, while the insert blocks 472 are correspondingly extended into the insert slots 242 so that the lens 2 is firmly embedded in the outer frame 1. Referring to FIG. 5, when the eye covering is worn in front of a wearer's eyes, the gasket 5 abuts against a facial area around the wearer's eyes to provide protection. Moreover, air in the covering space 6 flows out through each vent channel 8 from the corresponding inlet 83 to the corresponding outlet 84 in the direction indicated by the arrow "A." Air also flows into the covering space 6 through each lower vent channel 7 in the direction indicated by the arrow "B." The disposition of the vent channels 8 and the lower vent channels 7 enables air to freely flow into and out of the covering space 6 and prevents air from becoming trapped in the covering space 6. Trapped air may cause the temperature inside the covering space 6 to increase, which may be uncomfortable for a wearer. In addition, it may cause fog to form on the surface of the lens 2, which may block a wearer's line of sight, arising in a safety hazard. Accordingly, the eye covering improves the comfort and safety of a wearer.

In summary, to assemble the lens 2 and the outer frame 1 of the preferred embodiment of this invention, in addition to engaging each engaging unit 21 with the corresponding hole unit 411, extending each second tab 23 downward into the corresponding second slot 441, and extending the middle engaging member 24 downward into the middle engaging hole 471, each engaging piece 22 is extended rearwardly into the corresponding first slot 421. Accordingly, the lens 2 is firmly fixed in the outer frame 1 to resist forces from multiple directions.

In addition, the inner frame 3 forms a cushion between the outer frame 1 and the lens 2, and the vent channels 8 are formed between the outer frame 1 and the inner frame 3 to permit fluid communication between the covering space 6 at the rear of the lens 2 and the outside environment at the front of the lens 2. The lower vent channels 7 are formed between the bottom edge of the lens 2 and the outer frame 1. Accordingly, venting functionality is provided.

While the present invention has been described in connection with what is considered the most practical and preferred embodiment, it is understood that this invention is not limited to the disclosed embodiment but is intended to cover various arrangements included within the spirit and scope of the broadest interpretation to encompass all such modifications and equivalent arrangements.

What is claimed is:

1. An eye covering comprising:
    an outer frame for surrounding a facial area around a wearer's eyes, said outer frame including a lens frame that has a first upright wall, said first upright wall being formed with at least one first slot;
    a lens engaged in said lens frame, said lens including at least one engaging piece that extends rearward to engage said first slot; and
    an inner frame having a lining portion that is disposed to line a peripheral portion of said lens and that is disposed between said peripheral portion of said lens and said outer frame.

2. The eye covering as claimed in claim 1, wherein said engaging piece includes a first tab that extends horizontally and rearwardly to engage said first slot.

3. The eye covering as claimed in claim 2, wherein said lens includes a lens body engaged in said lens frame, said engaging piece further including a vertical support that extends upward from a top edge portion of said lens body, said first tab extending horizontally and rearwardly from said vertical support.

4. The eye covering as claimed in claim 1, wherein said first upright wall is disposed at an upper part of said lens frame and is formed with two of said first slots that are horizontally spaced apart from each other, said lens including two of said engaging pieces, each engaging a corresponding one of said first slots.

5. The eye covering as claimed in claim 1, wherein said lens and said outer frame cooperate to define a covering space, said inner frame and said outer frame cooperating to define at least one vent channel that communicates spatially with said covering space and an external environment of said eye covering, said vent channel including an inlet disposed at a rear side of said lens and an outlet disposed at a front side of said lens.

6. The eye covering as claimed in claim 5, wherein said outer frame further includes a gasket extending rearwardly and integrally from said lens frame for abutting against the facial area around the wearer's eyes.

7. The eye covering as claimed in claim 6, wherein said lens frame further has an upper encasing wall that extends forward from an upper part of said first upright wall, and an upper connecting wall that extends rearward from a lower part of said first upright wall and that is connected to said gasket,
    said lens including a lens body having a top edge portion that serves as said peripheral portion of said lens, said lining portion of said inner frame being disposed between said upper encasing wall and said top edge portion of said lens body, and having a bottom embedding face, and an embedding channel that is formed in said bottom embedding face, that opens downward, and that receives said top edge portion of said lens body, said lining portion further having a front face and at least one vent opening formed through said front face, said vent opening serving as said outlet of said vent channel.

8. The eye covering as claimed in claim 7, wherein:

said inner frame and said outer frame cooperate to define a plurality of said vent channels, and said front face of said lining portion is formed with a plurality of said vent openings therethrough that correspond respectively to said vent channels;

said lining portion and said first upright wall being formed with a rear passage-forming structure that forms rear passage portions of said vent channels, each of said rear passage portions having said inlet of the respective one of said vent channels;

said lining portion and said upper encasing wall being formed with an upper passage-forming structure that forms upper passage portions of said vent channels, each of said upper passage portions extending between a corresponding one of said rear passage portions and a corresponding one of said vent openings.

9. The eye covering as claimed in claim 8, wherein said rear passage-forming structure includes:

a plurality of first protruding face portions that protrude from one side of one of said lining portion and said first upright wall toward the other one of said lining portion and said first upright wall and that are horizontally spaced apart from each other;

a plurality of first indented face portions that are formed in said one side of said one of said lining portion and said first upright wall, each of said first indented face portions being adjacent to a corresponding one of said first protruding face portions and being indented away from the other one of said lining portion and said first upright wall; and a first abutment face that is disposed on one side of the other one of said lining portion and said first upright wall, that abuts against said first protruding face portions, and that cooperates with said first indented face portions to form said rear passage portions of said vent channels.

10. The eye covering as claimed in claim 8, wherein said upper passage-forming structure includes:

a plurality of second protruding face portions that protrude from one side of one of said lining portion and said upper encasing wall toward the other one of said lining portion and said upper encasing wall and that are horizontally spaced apart from each other; a plurality of second indented face portions that are formed in said one side of said one of said lining portion and said upper encasing wall, each of said second indented face portions being adjacent to a corresponding one of said second protruding face portions and being indented away from the other one of said lining portion and said upper encasing wall; and a second abutment face that is disposed on one side of the other one of said lining portion and said upper encasing wall, that abuts against said second protruding face portions, and that cooperates with said second indented face portions to form said upper passage portions of said vent channels.

11. The eye covering as claimed in claim 7, wherein said lens body further has two lateral bottom edge portions, said lens frame further having a pair of lower encasing walls each disposed below a corresponding one of said lateral bottom edge portions of said lens body, a pair of second upright walls each extending upward from a rearward part of a corresponding one of said lower encasing walls, and a pair of lower connecting walls each extending rearward from an upper part of a corresponding one of said second upright walls and being connected to said gasket, each of said lateral bottom edge portions of said lens body cooperating with a corresponding one of said lower encasing walls, a corresponding one of said second upright walls, and a corresponding one of said lower connecting walls to form a corresponding lower vent channel that communicates spatially with said covering space and the external environment of said eye covering.

12. The eye covering as claimed in claim 11, wherein: said lens frame further has a middle support wall in the form of a downwardly opening generally U-shaped body, said middle support wall being connected to said lower encasing walls, said second upright walls, and said lower connecting walls, a front upwardly extending wall that is connected to a front edge of said middle support wall and that has opposite ends connected to said lower encasing walls, respectively, and a rear protruding wall that extends upward from a top section of said middle support wall and that is disposed spacedly behind said front upwardly extending wall, said top section of said middle support wall being formed with a middle engaging hole disposed between said front upwardly extending wall and said rear protruding wall, said front upwardly extending wall cooperating with said rear protruding wall to form an engaging channel that is in spatial communication with said middle engaging hole;

said lens body further having a central bottom edge portion disposed between said lateral bottom edge portions and disposed between said front upwardly extending wall and said rear protruding wall, said central bottom edge portion being formed with a middle engaging member that extends into said middle engaging hole via said engaging channel.

13. The eye covering as claimed in claim 12, wherein said front upwardly extending wall extends upward and inclines rearward relative to said front edge of said middle support wall to abut against said lens body.

14. The eye covering as claimed in claim 12, wherein said middle support wall has a pair of insert blocks each extending upward from said top section of said middle support wall at a corresponding lateral side of said middle engaging hole, said front upwardly extending wall having a rear side formed with a guide channel, said central bottom edge portion of said lens body being formed with a pair of insert slots to engage said insert blocks respectively, said middle engaging member including an insert board part that is disposed between said insert slots, said insert board part having a front side formed with a projection, said projection extending into said guide channel and abutting against said front upwardly extending wall.

15. The eye covering as claimed in claim 11, wherein each of said lower encasing walls of said lens frame has a lateral end part formed with a second slot, said lens body further having a pair of second tabs each extending downward into said second slot in a corresponding one of said lower encasing walls.

16. The eye covering as claimed in claim 7, wherein said upper encasing wall of said lens frame has a pair of lateral end parts, each of which is formed with a corresponding hole unit, said lens body being formed with a pair of engaging units, each extending upward from said top edge portion of said lens body and through said lining portion of said inner frame to engage said hole unit in a corresponding one of said lateral end parts of said upper encasing wall.

17. The eye covering as claimed in claim 16, wherein each of said hole units is formed with a pair of top holes and a brace that separates said top holes, each of said engaging unit s being formed with a pair of prongs, each of said prongs being received in a corresponding one of said top holes, said brace of each of said hole units being received between said prongs of the corresponding one of said engaging units.

* * * * *